United States Patent [19]

Wagner

[11] 4,205,169
[45] May 27, 1980

[54] N-[4-AZIDO-5-(2-ETHOXYETHYL)-6-PHENYL-2-PYRIMIDINYL]ACETAMIDE AND CONGENERS

[75] Inventor: Hans A. Wagner, Skokie, Ill.

[73] Assignee: G. D. Searle & Co., Skokie, Ill.

[21] Appl. No.: 28,034

[22] Filed: Apr. 9, 1979

[51] Int. Cl.$^2$ .................. C07D 239/48; C07D 487/04
[52] U.S. Cl. .................................... 544/323; 544/254
[58] Field of Search ............................. 544/323, 254

[56] References Cited

U.S. PATENT DOCUMENTS

| 3,412,094 | 11/1968 | Rorig et al. | 544/323 |
| 3,455,921 | 6/1969 | Wagner | 544/323 |

Primary Examiner—Paul M. Coughlan, Jr.
Attorney, Agent, or Firm—John M. Brown

[57] ABSTRACT

Preparation and the diuretic utility of N-[4-azido-5-(2-ethoxyethyl)-6-phenyl-2-pyrimidinyl]acetamide and congeners are disclosed.

11 Claims, No Drawings

N-[4-AZIDO-5-(2-ETHOXYETHYL)-6-PHENYL-2-PYRIMIDINYL]ACETAMIDE AND CONGENERS

This invention relates to N-[4-azido-5-(2-ethoxyethyl)-6-phenyl-2-pyrimidinyl]acetamide and congeners, and to processes for the preparation thereof. More particularly, this invention provides new, useful, and unobvious chemical compounds of the formula

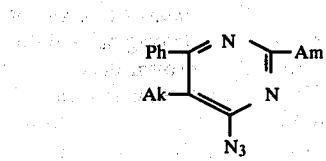

wherein Am represents (1-oxoalkyl)amino, [(alkylamino)carbonyl]amino, (alkoxycarbonyl)amino, or bis (alkoxycarbonyl)amino; Ak represents hydrogen, alkyl, hydroxyalkyl, alkoxyalkyl, alkenyl, or alkynyl; and Ph represents phenyl optionally substituted by 1 or more halogens, alkyls, alkoxys, and/or nitros.

Among the groupings represented by Am, those in which each of the constituent oxoalkyls, alkyls, and alkoxys contains fewer than 5 carbons are preferred, for example, formylamino, acetylamino, (1-oxopropyl)amino, (2-methyl-1-oxopropyl)amino, (1-oxobutyl)amino, diacetylamino, bis(1-oxopropyl)amino, bis(2-methyl-1-oxopropyl)amino, bis(1-oxobutyl)amino, [(methylamino)- carbonyl]amino, [(ethylamino)carbonyl]amino, {[(1-methylethyl)-amino]carbonyl}amino, {[(1,1-dimethylethyl)amino]carbonyl}-amino, [(propylamino)carbonyl]amino, {[(1-methylpropyl)amino]-carbonyl}amino, {[(2-methylpropyl)amino]carbonyl}amino, [(butylamino)carbonyl]amino, (methoxycarbonyl)amino, (ethoxycarbonyl)amino, [(1-methylethoxy)carbonyl]amino, [(1,1-dimethylethoxy)carbonyl]amino, (propoxycarbonyl)amino, [(1-methylpropoxy)carbonyl]amino, [(2-methylpropoxy)carbonyl]-amino, (butoxycarbonyl)amino, bis(methoxycarbonyl)amino, bis(ethoxycarbonyl)amino, bis[(1-methylethoxy)carbonyl]amino, bis[(1,1-dimethylethoxy)carbonyl]amino, bis(propoxycarbonyl)-amino, bis[(1-ethylpropoxy)carbonyl]amino, bis[(2-methylpropoxy)-carbonyl]amino, and bis(butoxycarbonyl)amino.

The groupings—as distinct from hydrogen—represented by Ak, like the oxoalkyls, alkyls, and alkoxys comprehended by Am, preferably contain fewer than 5 carbons, for example, methyl, ethyl, 1-methylethyl, 1,1-dimethylethyl, propyl, 1-methylpropyl, 2-methylpropyl, butyl, hydroxymethyl, 1-hydroxyethyl, 2-hydroxyethyl, 1-hydroxy-1-methylethyl, 2-hydroxy-1-methylethyl, 2-hydroxy-1,1-dimethylethyl, 1-hydroxypropyl, 2-hydroxypropyl, 3-hydroxypropyl, 1-hydroxy-1-methyl-propyl, 2-hydroxy-1-methylpropyl, 3-hydroxy-1-methylpropyl, 1-(hydroxymethyl)propyl, 1-hydroxy-2-methylpropyl, 2-hydroxy-2-methylpropyl, 3-hydroxy-2-methylpropyl, 1-hydroxybutyl, 2-hydroxybutyl, 3-hydroxybutyl, 4-hydroxybutyl, methoxymethyl, ethoxymethyl, (1-methylethoxy)methyl, propoxymethyl, 1-methylethyl, 2-methylethyl, 1-ethoxyethyl, 2-ethoxyethyl, 1-methylpropyl, 2-methylpropyl, 3-methylpropyl, ethenyl, 1-methylethenyl, 1-propenyl, 2-propenyl, 1-butenyl, 2-butenyl, 3-butenyl, ethynyl, 1-propynyl, 2-propynyl, 1-butynyl, 2-butynyl, and 3-butynyl, among which alkoxyalkyl groupings such as ethoxymethyl, 1-methoxyethyl, 2-methoxyethyl, 1-ethoxyethyl, 2-ethoxyethyl, and 3-methoxypropyl are especially advantageous.

When Ph in Formula I represents substituted phenyl, from 1 to 3 substituents are typical, althouugh as many as 5 are within the purview of the invention. Among these substituents, alkyls and alkoxys containing fewer than 5 carbons (such as those specified above) and halogens characterized by atomic numbers less than 53 (i.e., fluorine, chlorine, and bromine) are preferred. The position of the substituents on the benzene ring relative to its attachment to the pyrimidine nucleus is not critical; and more than 1 type of substituent (for example, alkyl and halogen) can be advantageously present.

Those skilled in the art will recognize that 4-azidopyrimidines are disposed, under favorable conditions, to participate in the so-called azidomethine-tetrazole equilibrium. [Temple et al., J. Org. Chem., 30, 829 (1965)]. The tetrazolo constituents of such an equilibrium mixture involving the instantly disclosed azidopyrimidines have the formula

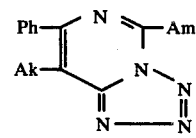

wherein Am, Ak, and Ph retain the meanings previously assigned; and the relative amounts of the 2 tautomeric forms of the subject compounds in existence under any given circumstance are dependent upon the physical state of the involved substances and their environment—whether they be solid or liquid, and, if dissolved, in what solvent, at what temperature, and at what PH. Because the various forms in which tautomers exist cannot readily be represented by a single formula, the subject compounds are named and enformulated exclusively as azides for convenience only; both azido and tetrazolo forms, notwithstanding, are within the ambit of the described invention.

The compounds to which this invention relates are useful because of their valuable pharmacological properties. Thus, for example, they are exceptionally potent diuretics: When assayed for the capacity to increase urine volume as described by Lipschitz et al. [J. Pharmacol. Exp. Therap., 79, 97 (1943)] and assigned potencies based upon parallel dose response curves in accordance with Finney (Statistical Method in Biological Assay, 2nd ed., Charles Griffin & Company, Limited, London, 1964], N-[4-azido-5-(2-ethoxyethyl)-6-phenyl 2-pyrimidinyl]acetamide, N-acetyl-N-[4-azido-5-(2-ethoxyethyl)-6-phenyl-2-pyrimidinyl]acetamide, and diethyl [4-azido-5-(2-ethoxyethyl)-6-phenyl-2-pyrimidinyl]imidodicarbonate were found to be 9.4, 23.4, and 5.8 times as potent as dihydrochlorothiazide, respectively. Distinct both structurally and pharmacologically, 4-azido-5-(2-ethoxyethyl)-6-phenyl-2-pyrimidinamine was found to be only 1.4 times as potent as dihydrochlorothiazide when identically assayed.

For therapeutic purposes, the compounds of this invention are ordinarily combined with one or more adjuvants appropriate to the indicated route of administration. If per os, they may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and thus tableted or encapsulated for convenient administration; alternatively, they may be dissolved in water or a comparably innocuous liquid. Parenteral administration may be effected via sterile fluid admixture with water, polyethelene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art; see, for example, F. W. Martin et al., "Remington's Pharmaceutical Sciences", 14th ed., Merck Publishing Co., Eaton, Pa., 1965.

Appropriate dosages, in any given instance, of course depend upon the nature and severity of the condition treated, the route of administration, and the species of mammal involved, including its size and any individual idiosyncrasies which obtain.

The amides of this invention can be prepared by contacting, individually in pyridine at around 25° C., 2-aminopyrimidines of the formula

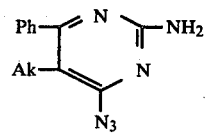

III (wherein Ak and Ph are defined as above) with alkanoic acid anhydrides and separating the 2-(1-oxoalkyl)amino and 2-[bis(1-oxyalkyl)amino]products which result in each instance by fractional crystallization. As an exception to this procedure, the formamides of this invention can be prepared by contacting, individually at around 25° C., the 2-aminopyrimidines of Formula III with the mixed anhydride of acetic and formic acids. If the Formula III starting material contains a 5-hydroxyalkyl substituent, the hydroxyl therein is esterified during the foregoing procedures but the ester is readily saponifiable via appropriately prolonged contact with potassium carbonate in aqueous methanol at around 25° C.

The ureas of this invention can be prepared by contacting, individually in pyridine at around 25° C., the 2-aminopyrimidines of Formula III with isocyanatoalkanes.

The dialkyl imidodicarbonates of this invention can be prepared by contacting, individually in pyridine at around 25° C., the 2-aminopyrimidines of Formula III with dialkyl dicarbonates.

And, finally, the carbamates of this invention can be prepared by heating the dialkyl imidodicarbonates of this invention, individually in aqueous methanol, with potassium bicarbonate.

The following examples describe in detail compounds illustrative of the present invention and methods which have been devised for their preparation. However, the invention is not to be construed as limited thereby, either in spirit or in scope, since it will be apparent to those skilled in the art of organic synthesis that many modifications, both of materials and of methods, may be practiced without departing from the purpose and intent of this disclosure. Throughout the examples hereinafter set forth, temperatures are given in degrees centigrade and relative amounts of materials in parts by weight, except as otherwise noted.

EXAMPLE 1

To a solution of 14 parts of 4-azido-5-(2-ethoxyethyl)-6-phenyl-2-pyrimidinamine (U.S. Pat. No. 3,412,094) in 105 parts of 98% formic acid is added, with stirring during 70 minutes, 35 parts of acetic acid anhydride. The resultant solution is allowed to stand at room temperature for 48 hours, then stirred into 1200 parts of ice-cold water. The mixture thus obtained is allowed to stand at room temperature overnight, whereupon insoluble solids are filtered off, washed with cold water, dried in vacuo at 30° under nitrogen overnight, and thereupon extracted with approximately 350 parts of boiling 1,1'-oxybisethane. The extract is concentrated by distillation to about 20% of its original volume, following which the precipitate thrown down is filtered off and dried in air. The product thus isolated is N-[4-azido-5-(2-ethoxyethyl)-6-phenyl-2-pyrimidinyl]formamide melting at approximately 105°–106°. It has the formula

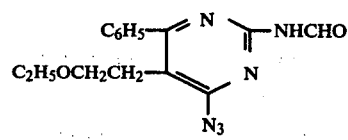

EXAMPLE 2

To a solution of approximately 28 parts of 4-azido-5-(2-ethoxyethyl)-6-phenyl-2-pyrimidinamine in 100 parts of pyridine is added, with stirring, 51 parts of acetic acid anhydride. The resultant solution is allowed to stand at room temperatures for 72 hours, then stripped of liquid by vacuum distillation at around 25°. The distilland is taken up in 200 parts of dichloromethane. The dichloromethane extract is washed with cold water, dried over anhydrous sodium sulfate, filtered, mixed with decolorizing charcoal, again filtered, and finally stripped of solvent by vacuum distillation. The residue is taken up in 250 parts of boiling 1,1'-oxybisethane. The resultant solution is allowed to stand at room temperatures for 18 hours, whereupon insoluble solids are filtered out and dried in air. The product thus isolated is N-[4-azido-5-(2-ethoxyethyl)-6-phenyl-2-pyrimidinyl]acetamide melting at approximately 132°–133°. It has the formula

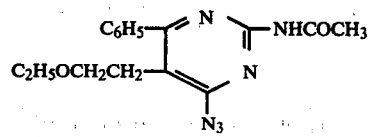

The oxybisethane mother liquor is concentrated to approximately 40% of its original volume by distillation, then mixed with an equal volume of pentane. The resultant mixture is chilled to around 5°. The precipitate which forms is filtered off and dried. The product thus isolated is N-acetyl-N-[4-azido-5-(2-ethoxyethyl)-6-phenyl-2-pyrimidinyl]-acetamide melting at approximately 78°–79°. It has the formula

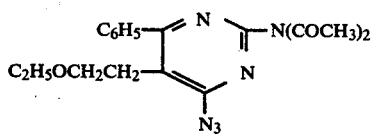

EXAMPLE 3

To a solution of 9 parts of 4-azido-5-(2-ethoxyethyl)-6-phenyl-2-pyrimidinamine in 100 parts of pyridine is added, with stirring, 39 parts of propanoic acid anhydride. The resultant solution is, consecutively, allowed to stand at room temperatures for 24 hours, stirred at 60° for 3 hours, allowed to stand again at room temperatures for 16 hours, and stripped of liquid by vacuum distillation at 40°. The residue is stirred with 100 parts of water at room temperatures for 3 hours, and the resultant mixture is extracted with 500 parts of 1,1'-oxybisethane. The oxybisethane extract is consecutively washed with aqueous 5% sodium bicarbonate and cold water, dried over anhydrous sodium sulfate, filtered, mixed with decolorizing charcoal, again filtered, and finally concentrated to about 7% of its original volume by distillation. The concentrate is diluted with 25 parts of pentane. The precipitate which forms, isolated by filtration and dried in air, is N-[4-azido-5-(2-ethoxyethyl)-6-phenyl-2-pyrimidinyl]-propanamide melting at approximately 90°. The product has the formula

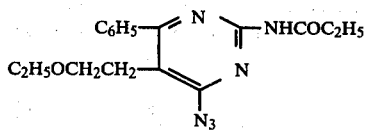

The oxybisethane-pentane mother liquor is concentrated to approximately 40% of its original volume by distillation, then diluted to the point of incipient precipitation by stirring in hexane. The resultant mixture is chilled to around 5°. The precipitate which forms is filtered off and dried in air. The product thus isolated is N-[4-azido-5-(2-ethoxyethyl-6-phenyl-2-pyrimidinyl]-N-(1-oxopropyl)propanamide. It has the formula

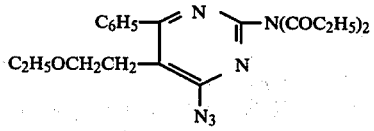

EXAMPLE 4

Substitution of 56 parts of 2-methylpropanoic acid anhydride for the propanoic acid anhydride called for in Example 3 affords, by the procedure there detailed, N-[4-azido-5-(2-ethoxyethyl)-6-phenyl-2-pyrimidinyl]-2-methylpropanamide, having the formula

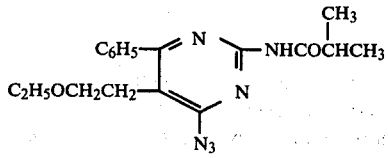

and N-[4-azido-5l -(2-ethoxyethyl)-6-phenyl-2-pyrimidinyl]-2-methyl-N-(1-oxo-2-methylpropyl)-propanamide, having the formula

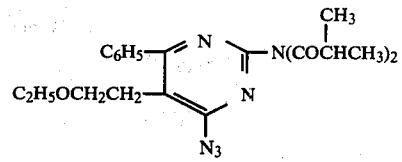

EXAMPLE 5

To a solution of 85 parts of 4-azido-5-(2-ethoxyethyl)-6-phenyl-2-pyramidinamine in 750 parts of pyridine is added 105 parts of isocyanatomethane. The resultant solution is stirred for 7 hours at room temperatures, then allowed to stand at room temperatures for 53 hours, whereupon 200 parts of methanol is introduced and stirring resumed for 2 hours. The solution thus obtained is poured into 5000 parts of ice-cold water. The resultant mixture is stirred at 0°-5° until a granular solid precipitates. The precipitate is separated by filtration, washed with water, dried in air, and recrystallized from 1,1'-oxybisethane to afford N-[4-azido-5- (2-ethoxyethyl)-6-phenyl-2-pyrimidinyl]-N'-methylurea melting at 128°-130°. The product has the formula

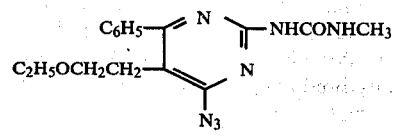

EXAMPLE 6

Substitution of 148 parts of 1-isocyanato-1,1-dimethylethane for the isocyanatomethane called for in Example 5 affords, by the procedure there detailed, N-[4-azido-5-(2-ethoxyethyl)-6-phenyl-2-pyrimidinyl]-N'-(1,1-dimethylethyl)urea. The product has the formula

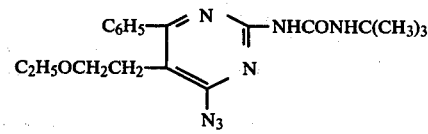

EXAMPLE 7

To a solution of approximately 14 parts of 4-azido-5-(2-ethoxyethyl)-6-phenyl-2-pyrimidinamine in 100 parts of pyridine is added, with stirring during the course of 1 hour, 68 parts of dimethyl dicarbonate. The resultant solution is allowed to stand at room temperatures for 1 hour, then stripped of solvent by vacuum distillation. The residue is extracted with methylbenzene; and the extract is chromatographed on silica gel, using methylbenzene and mixtures thereof with increasing amounts of ethyl acetate as developing solvents. From eluates identified by thin layer chromatography as containing substantial amounts of dimethyl [4-azido-5-(2-ethoxyethyl)-6-phenyl-2-pyrimidinyl]imidodicarbonate, combined and stripped of solvent by vacuum distillation, the aforesaid product is isolated. It has the formula

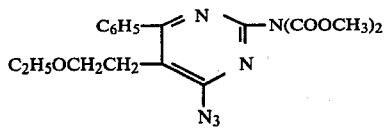

EXAMPLE 8

Substitution of 81 parts of diethyl dicarbonate for the dimethyl dicarbonate called for in Example 7 affords, by the procedure there detailed, diethyl [4-azido-5-(2-ethoxyethyl)-6-phenyl-2-pyrimidinyl]imidodicarbonate. Further purified by recrystallization from a mixture of 1,1'-oxybisethane and pentane, the product melts at approximately 37°–38°. It has the formula

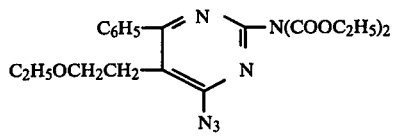

EXAMPLE 9

Substitution of 110 parts of di(1,1-dimethylethyl) dicarbonate for the dimethyl dicarbonate called for in Example 7 affords, by the procedure there detailed, bis(1,1-dimethylethyl) [4-azido-5-(2-ethoxyethyl)-6-phenyl-2-pyrimidinyl]imidodicarbonate. The product has the formula

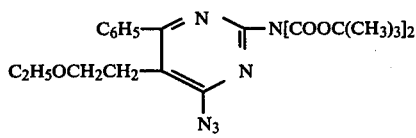

EXAMPLE 10

To a solution of 4 parts of dimethyl [4-azido-5-(2-ethoxyethyl)-6-phenyl-pyrimidinyl]imidodicarbonate in 40 parts of methanol is added a solution of 1 part of potassium bicarbonate in 10 parts of water. The resultant solution is heated at the boiling point under reflux for 5 hours, then allowed to stand at room temperatures overnight. Approximately 1 part of acetic acid is introduced at this point, whereupon liquids are removed by vacuum distillation. The residue is partitioned between 1,1'-oxybisethane and water. The aqueous phase is discarded, whereas the ethereal phase is dried over anhydrous sodium sulfate, filtered, and stripped of solvent by distillation. The residue is methyl [4-azido-5-ethoxyethyl)-6-phenyl-2-pyrimidinyl]carbamate, which is further purified by recrystallization from a mixture of 1,1-oxybisethane and pentane. The product has the formula

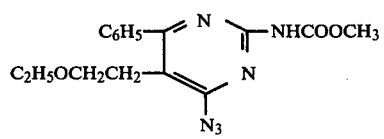

EXAMPLE 11

Substitution of 4 parts of diethyl [4-azido-5-(2-ethoxyethyl)-6-phenyl-2-pyrimidinyl]imidodicarbonate for the dimethyl [4-azido-5-(2-ethoxyethyl)-6-phenyl-2-pyrimidinyl]-imidodicarbonate called for in Example 10 affords, by the procedure there detailed, ethyl [4-azido-5-(2-ethoxyethyl)-6-phenyl-2-pyrimidinyl]carbamate melting at approximately 103°–103.5°. The product has the formula

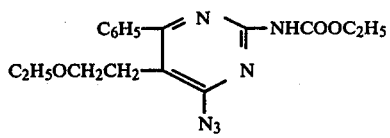

EXAMPLE 12

Substitution of 4 parts of bis(dimethylethyl) [4-azido-5-(2-ethoxyethyl-6-phenyl-2-pyrimidinyl]imidodicarbonate for the dimethyl [4-azido-5-(2-ethoxyethyl-6-phenyl-2-pyrimidinyl]imidodicarbonate called for in Example 10 affords, by the procedure there detailed, (1,1-dimethylethyl) [4-azido-5-(2-ethoxyethyl)-6-phenyl-2-pyrimidinyl]carbamate, having the formula

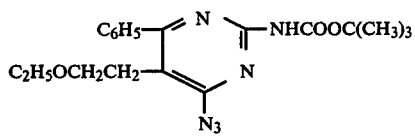

What is claimed is:
1. A compound of the formula

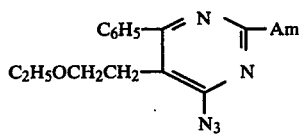

wherein Am represents (1-oxoalkyl)amino, bis(1-oxoalkyl)amino, [(alkylamino)carbonyl]amino, (alkoxycarbonyl)amino, or bis(alkoxycarbonyl)amino in which each of the constituent oxoalkyls, alkyls, and alkoxys contains fewer than 5 carbons.

2. A compound according to claim 1 having the formula

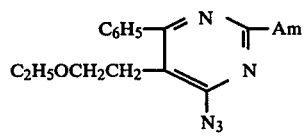

wherein Am represents (1-oxoalkyl)amino in which the oxoalkyl contains fewer than 5 carbons.

3. A compound according to claim 1 which is N-[4-azido-5-(2-ethoxyethyl)-6-phenyl-2-pyrimidinyl]acetamide.

4. A compound according to claim 1 having the formula

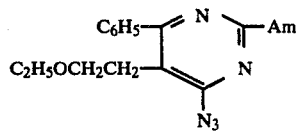

wherein Am represents bis(1-oxoalkyl)amino in which each oxoalkyl contains fewer than 5 carbons.

5. A compound according to claim 1 which is N-acetyl-N-[4-azido-5-(2-ethoxyethyl)-6-phenyl-2-pyrimidinyl]-acetamide.

6. A compound according to claim 1 having the formula

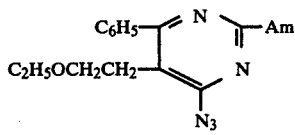

wherein Am represents [(alkylamino)carbonyl]amino in which the alkyl contains fewer than 5 carbons.

7. A compound according to claim 1 which is N-[4-azido-5-(2-ethoxyethyl)-6-phenyl-2-pyrimidinyl]-N'-methylurea.

8. A compound according to claim 1 having the formula

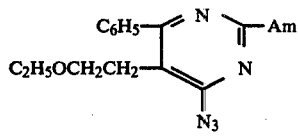

wherein Am represents (alkoxycarbonyl)amino in which the alkoxy contains fewer than 5 carbons.

9. A compound according to claim 1 which is ethyl [4-azido-5-(2-ethoxyethyl)-6-phenyl-2-pyrimidinyl]carbamate.

10. A compound according to claim 1 having the formula

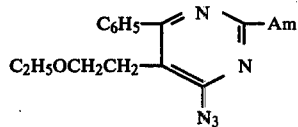

wherein Am represents bis(alkoxycarbonyl)amino in which each alkoxy contains fewer than 5 carbons.

11. A compound according to claim 1 which is diethyl [4-azido-5-(2-ethoxyethyl)-6-phenyl-2-pyrimidinyl]imidodicarbonate.

* * * * *